US006457441B1

(12) United States Patent
Uchiyama

(10) Patent No.: US 6,457,441 B1
(45) Date of Patent: Oct. 1, 2002

(54) SUPERHEATED STEAM APPARATUS

(75) Inventor: Mitsuru Uchiyama, Funabashi (JP)

(73) Assignee: Medical Clean Products Inc., Chiba (JP)

( * ) Notice: Subject to any disclaimer, the term of this patent is extended or adjusted under 35 U.S.C. 154(b) by 0 days.

(21) Appl. No.: 09/772,970

(22) Filed: Jan. 31, 2001

(51) Int. Cl.[7] .................................................. A61L 2/06

(52) U.S. Cl. ............................ 122/459; 422/22; 422/26

(58) Field of Search ................................. 122/396, 429, 122/459, 508, 5.52; 204/660; 422/26, 298, 299, 22

(56) References Cited

U.S. PATENT DOCUMENTS 4,263,258 A * 4/1981 Kalasek ........................ 422/26
6,006,009 A * 12/1999 Friedheim ................ 122/479.1
6,264,543 B1 * 7/2001 Garcia et al. ............... 452/141

* cited by examiner

*Primary Examiner*—Gregory Wilson
(74) *Attorney, Agent, or Firm*—Finnegan, Henderson, Farabow, Garrett & Dunner, LLP

(57) ABSTRACT

This invention provides a superheated steam apparatus that is cable of efficiently heating water to generate superheated steam, and to perform a process such as sterilization utilizing this superheated steam while keeping the loss of heating energy to a minimum.

The invention comprises a processing section 11 at the top on the inside of a housing container 2, which is at atmospheric pressure, for performing a process utilizing superheated steam, and where the processing section 11 includes a steam discharge outlet 12, and a superheated steam generation section 10 located at the bottom of the processing section 11; and where the superheated steam generation section 10 generates superheated steam or moist air inside the housing container 2, hat is essentially in an open state, and is connected with the processing section 11 in an open state.

4 Claims, 2 Drawing Sheets

12
1
2
D
11
3
4
7
6
9
C
10
Water
8
Gas Fuel
5
A
B
Air

SUPERHEATED STEAM APPARATUS

BACKGROUND OF THE INVENTION

1. Field of the Invention

This invention relates to a superheated steam apparatus for processes such as sterilization, food preparation or the like, which use superheated steam that is generated from water vapor at atmospheric pressure.

2. Description of the Related Art

Superheated steam is used for sterilization for example. When superheated steam is used at normal pressure or atmospheric pressure, it is not necessary to have a structure for high pressure such as a high-pressure boiler or high-pressure container, so construction of the facility or equipment is simplified and safety increases and the need for regulatory inspection or control becomes unnecessary or becomes simplified.

A sterilization apparatus using this kind of superheated steam at atmospheric pressure has been disclosed in U.S. Pat. No. 4,263,258. This sterilization apparatus comprises a heat-insulated container that is filled with a heat-transfer medium and also is equipped with a sterilization chamber, and a water conduit through which the heat-transfer medium passes, and is capable of heating the heat-transfer medium to 100° C. or greater. The water conduit comprises an evaporation section for converting the water into steam, and a steam-heating section for converting the steam into superheated steam, and it is connected to the sterilization chamber. The water that is supplied by way of the water conduit is vaporized in the conduit to become steam, and then is further heated to become superheated steam. This superheated steam is supplied to the inside of the sterilization chamber from one end of the water conduit where it sterilizes the object inside the chamber.

However, in the sterilization apparatus described above, there is a water conduit located inside the heat-insulated container, and this water conduit is heated by the heat-transfer medium, whereby the water in the water conduit is vaporized to steam and then the steam is further heated inside the water conduit until it becomes superheated steam, after which this superheated steam is then further directed through the water conduit to the sterilization chamber, so there is large heat loss of the heat-transfer path to the inside of the water conduit and heating energy is not efficiently used for generating superheated steam and is wasted.

SUMMARY OF THE INVENTION

Taking the problems of the related art into consideration, the object of this invention is to provide a superheated steam apparatus that is capable of efficiently heating water to generate superheated steam, and to perform a process such as sterilization utilizing this superheated steam while keeping the loss of heating energy to a minimum.

In order to accomplish the object above, this invention provides a superheated steam apparatus comprising; a processing section at the top on the inside of a housing container, which is at atmospheric pressure, for performing a process utilizing superheated steam and which includes a steam discharge outlet, and a superheated steam generation section located at the bottom of the processing section; and where the superheated steam generation section generates superheated steam or moist air inside the housing container, that is essentially in an open state, and is connected with the processing section in an open state.

With this construction, superheated steam is generated inside the housing container in an open state. In other words, the superheated steam that is generated is not enclosed in a separate sealed space inside the conduit inside the container or in the container, but actually spreads and fills the entire inside of the container. This superheated steam generation section is not separated from the processing section at the top but is connected, and the superheated steam enters the processing section in an open state. That is, the superheated steam generation section and the processing section are not separated at all, or in the case that they are separated, there is plenty of open area for sufficient circulation such that neither the heat loss nor resistance to flow are affected. For example, the sections may be separated by the support plate of the object to be processed or by a partition, and the superheated steam that is generated enters the processing section where processing such as sterilization or cooking is performed, without heat loss or flow resistance.

In this case, depending on the purpose of the apparatus or the operating conditions, it is possible for the superheated steam generation section to generate moist air that is 100° C. instead of steam in the superheated region that is 100° C. or greater. Depending on the purpose, it is possible to obtain sufficient sterilization results by using this kind of moist air as well. In doing so, it is possible to conserve energy.

In one form of the invention, as the aforementioned superheated steam generation section combusts and burns the fuel, the combusted gas is mixed with the steam when generating the superheated steam.

With this construction, the fuel is combusted in steam at atmospheric pressure, and by mixing this high-temperature combusted gas with steam, the steam is heated above 100° C. to generate superheated steam, so hardly any of the thermal energy of the combusted gas is lost, and can immediately be used for superheating the steam, thus making it possible to efficiently heat the steam to obtain superheated steam.

In another form of the invention, the open steam generation section is located at the bottom of the aforementioned housing container, the superheated steam generation section is located above this steam generation section, and this superheated steam generation section mainly heats the steam through radiation heating to generate superheated steam.

With this construction, steam is generated in an open state inside the housing container, and then this steam is heated as is in an open state inside the container to above 100° C. through radiation heating, such as by a heating lamp, thus the thermal energy is used efficiently for superheating, making it possible obtain superheated steam with hardly any heat loss.

In yet another form of the invention, there is a means for forming minute water particles, and the minute water particles that are formed through this means are heated to produce steam, and this steam is then further heated to generate superheated steam.

With this construction, mist made up of minute water particles is formed using an oscillator, such as that is used in a quartz resonator, or a sprayer, and steam is obtained by heating these minute water particles. Moreover, the spherical minute water particles absorb thermal energy, making it possible to efficiently generate steam.

DESCRIPTION OF THE PREFERRED EMBODIMENTS

The preferred embodiments of the invention will be explained with reference to the drawings.

Figure 1:
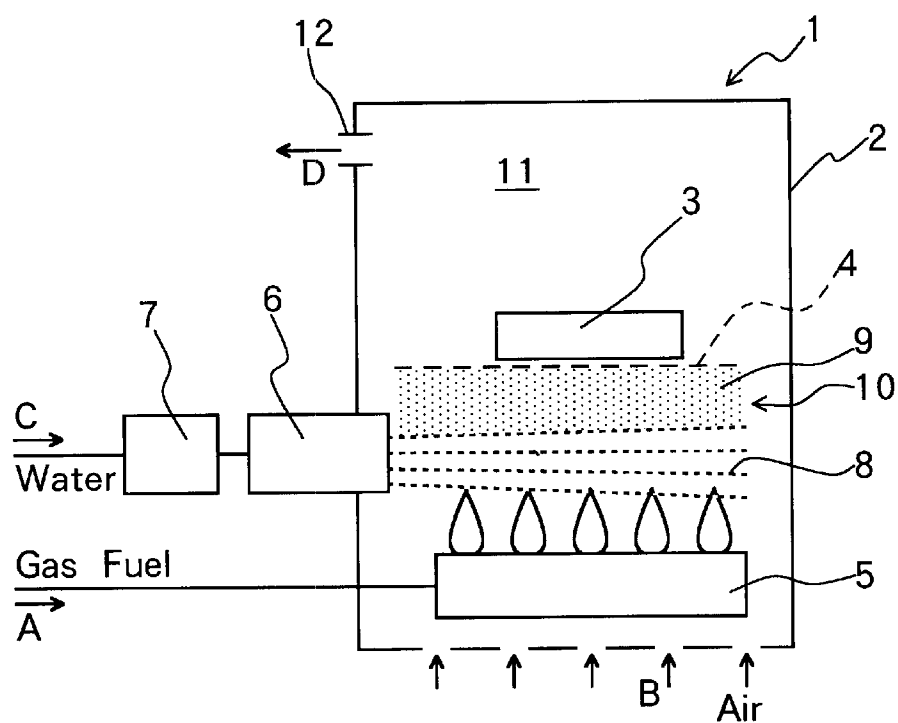
FIG. 1 is a schematic diagram explaining an embodiment of the invention.

FIG. 1 is a schematic drawing of a sterilization apparatus related to an embodiment of the invention.

The outer frame of this sterilization apparatus 1 is completely formed by a housing container. A processing section 11 for performing sterilization is formed at the top of the housing container 2, and the object 3 to be sterilized is placed on a support member 4. There is a combustor 5 at the bottom of the housing container 2, to which gas fuel is supplied in the direction of the arrow A. The container 2 around the area of the combustor 5 is open to the outside, or there is an air intake that allows air into the container in the direction of the arrow B such that the gas fuel can burn.

There is an oscillator 6 having a quartz resonator or the like inside the housing 2 at the top of the combustor 5 or near it. This oscillator 6 converts the water that is supplied in the direction of the arrow C and heated by a heater 7, into minute water particles 8. These minute water particles 8 are supplied to the top of the combustor 5 and heated by the combusted gas. In this way, the minute water particles 8 are converted to steam. This steam is then further heated by the combusted gas to become superheated steam 9. The minute water particles 8 are supplied to or above the combustion flame of the combustor 5 inside the container in an open state. The steam and superheated steam, that are generated as the minute water particles 8 are converted by the heat from the combusted gas, similarly completely fill above the combustor 5 inside the open housing container 2. In this way, an open superheated steam generation section 10 is formed inside the housing container 2 above the combustor 5.

It is preferred that the aforementioned combusted gas be a combusted liquid or gas fuel or natural gas containing carbon (C) and hydrogen (H). For example, a combusted liquid fuel or combustible gas such as a kind of alcohol like ethyl alcohol (C2H5OH), methyl alcohol (CH3OH), propyl alcohol (C3H7OH), or butyl alcohol (C4H9OH), or propane (C3H8), or butane (C4H10), or a combusted natural gas of which the main component is a hydrocarbon. This combusted gas mixes with and heats the steam. There is mainly only carbon dioxide (CO2) and water (H2O) contained in the combusted gas, so even when it is mixed with superheated steam it does not affect sterilization or cause problems when used in cooking. Combustion also includes catalytic combustion.

This superheated steam is directed to the processing section 11 at the top of the container as is with hardly any heat loss or flow resistance. In other words, it flows upward with hardly any heat loss or resistance to flow in an open state without conduits or the like to the connected processing section 11 in the container, through natural heat convection or by the ventilation action of a ventilation fan (not shown in the drawings) that is located in the processing section 11. In this case, the partition or support member 4 on which the object 3 to be sterilized is placed, that is located between the superheated steam generation section 10 and the processing section 1 above it, is formed such that it has a sufficiently large opening for the superheated steam to freely pass through.

The top surface of the side surface of the processing section 11 may be open to the outside such that steam is constantly vented out, or the processing section 11 may be closed in by a cover (not shown in the drawings) that can be opened or closed. In the case that the processing section 11 is closed in by a cover, a ventilation vent 12 is located at a suitable location and the steam that fills the processing section 11 is constantly vented to the outside in the direction of the arrow D in order to maintain a constant flow of steam inside the processing section 11. In order to accomplish this, a fan may be used in the ventilation vent 12 (not shown in the drawings). By having the superheated steam constantly flow through the processing section 11 in this way, the enthalpy of the steam is maintained and it is possible to obtain sufficient sterilization.

It is also possible to insert hands into the processing section 11 to sterilize and disinfect hands and fingers. Superheated steam completely fills the processing section 11 such that it surrounds the hands and fingers, so it is possible to reduce the germs and bacteria that are adhered to the hands and fingers in a very short period of time. In this case, since a person's hands and fingers have thermal inertia, they do not feel hot or become burned even when surrounded by superheated steam.

Figure 2:
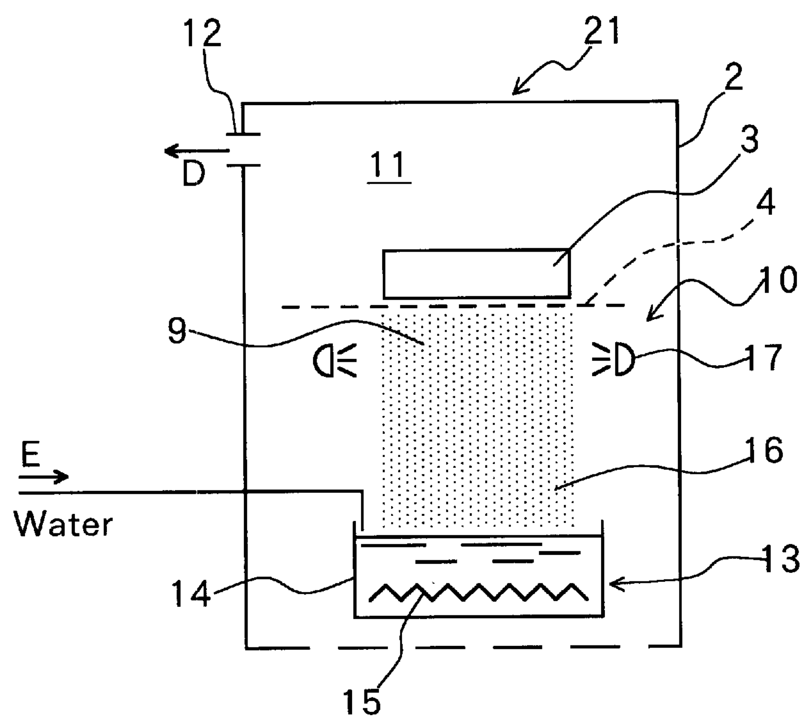
FIG. 2 is a schematic diagram explaining another embodiment of the invention.

FIG. 2 is a schematic diagram of another embodiment of the invention.

The sterilization apparatus 21 of this embodiment has an evaporation container 14 underneath the housing container 2 for containing water. There is an electric heater 15 in the evaporation container 14, and water is supplied to the container as shown by the arrow E. This evaporation container 14 comprises a steam generation section 13 which generates steam 16 in an open state inside the housing container 2. This steam 16 is heated by a carbon lamp 17 that is located at the top of the evaporation container 14 and converted to superheated steam 9. The carbon lamp 17 heats the steam by radiation heating with light having a wavelength that is easily absorbed by the water (steam), to form superheated steam. It is also possible to use another kind of heating lamp or a heater that is capable of radiant heating instead of the carbon lamp 17. By heating the steam in this way by radiant heat, it is possible to efficiently generate superheated steam inside an open space. As in the previously described embodiment, the superheated steam is led to the processing section 11 where it sterilizes the object 3 to be sterilized.

Figure 3:
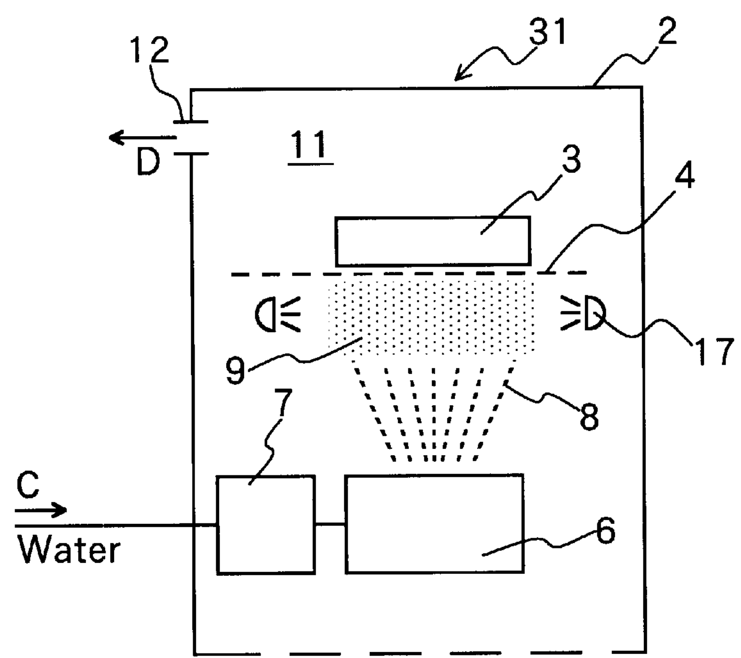
FIG. 3 is a schematic diagram explaining yet another embodiment of the invention.

FIG. 3 is a schematic diagram of yet another embodiment of the invention.

The sterilization apparatus 31 of this embodiment uses an oscillator 6 similar that in the embodiment described in FIG. 1 to generate minute water particles 8, and then heats these minute water particles by a carbon lamp 17 to cause-evaporation and form superheated steam.

By using an oscillator 6 to convert water (preferably hot water) to minute water particles and then heating those water particles to form steam, the spherical minute water particles absorb thermal energy over the entire spherical surface and use that thermal energy efficiently to become steam. This makes it possible to efficiently generate steam at atmospheric pressure with little energy. The steam at atmosphere pressure that is obtained in this way is then further heated by the carbon lamp 17 to become superheated steam, which is then led to the processing section 11.

In order to convert the water to minute water particles, it is possible to use a spray-type humidifier or other type of spray nozzle instead of an oscillator. The other construction and function are the same as those for the other embodiments described above.

Figure 4:
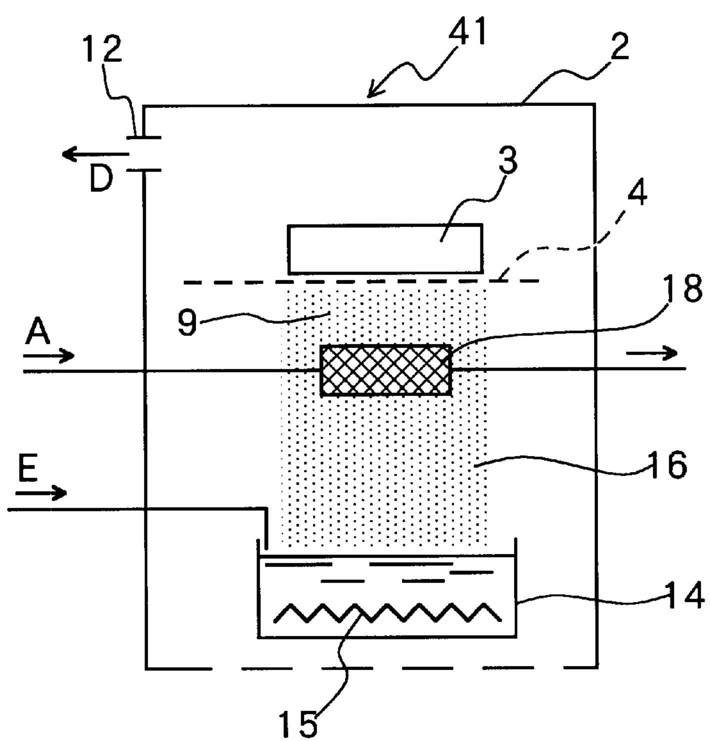
FIG. 4 is a schematic diagram explaining further yet another embodiment of the invention.

FIG. 4 is a schematic diagram showing further yet another embodiment of the invention.

The sterilization apparatus 41 of this embodiment uses an evaporation container 14 that is similar to that used in the embodiment shown in FIG. 2 to generate steam 16, and then heats this steam 16 by a catalyst 18 to form superheated steam 9. A gas fuel or the like is supplied to the catalyst as shown by the arrow A, to generate heat by way of a catalytic reaction. The other construction and function are the same as in the embodiments described above.

The oscillator for generating minute water particles, and the combusted gas, carbon lamp, electric heater, catalyst or the like for generating steam and superheated steam used in the embodiments described above can be combined in configurations other than those of the aforementioned embodiments, in order to construct a sterilization aparatus for generating superheated steam.

It is possible to use the processing section 11 of the housing container 2 as a heating apparatus and apply this invention to a cooking apparatus. It is also possible to use the processing section 11 as a radiant heat source and apply the invention to a radiation heating apparatus for heating.

With this invention, constructed as described above, superheated steam is generated inside a housing container that is open, and this superheated steam enters a processing section with hardly any heat loss or resistance to flow, so there is no need for a water conduit or the like and construction becomes simplified, as well as it becomes possible to efficiently utilize thermal energy to generate superheated steam with little energy, and to use that superheated steam to perform processing such as sterilization.

What is claimed is:

1. A superheated steam apparatus comprising:

a processing section at the top on the inside of a housing container, which is at atmospheric pressure, for performing a process utilizing superheated steam, and which includes;

a steam discharge outlet, and a superheated steam generation section located at the bottom of said housing container, wherein said superheated steam generation section generates superheated steam or moist air inside said housing container, that is essentially in an open state, and is connected with said processing section in an open state.

2. A superheated steam apparatus comprising:

a processing section at the top on the inside of a housing container, which is at atmospheric pressure, for performing a process utilizing superheated steam, and which includes;

a steam discharge outlet; and a superheated steam generation section located at the bottom of said housing container, wherein said superheated steam generation section generates superheated steam or moist air inside said housing container, that is essentially in an open state, and is connected with said processing section in an open state, and wherein said superheated steam generation section combusts and burns fuel, and the combusted gas is mixed with the steam when generating the superheated steam.

3. A superheated steam apparatus comprising:

a processing section at the top on the inside of a housing container, which is at atmospheric pressure, for performing a process utilizing superheated steam, and which includes, a steam discharge outlet; and a superheated steam generation section located at the bottom of said housing container, wherein said superheated steam generation section generates superheated steam or moist air inside said housing container, that is essentially in an open state, and is connected with said processing section in an open state, and wherein an open steam generation section is also located at the bottom of said housing container, said superheated steam generation section is located above said steam generation section, and said superheated steam generation section mainly heats the steam through radiation heating to generate superheated steam.

4. The superheated steam apparatus of any one of claims 1, 2 or 3 further comprising:

a means for forming minute water particles, and wherein the minute water particles, that are formed through said means of generating minute water particles, are heated to produce steam, and this steam is then further heated to generate superheated steam.

* * * * *

UNITED STATES PATENT AND TRADEMARK OFFICE

CERTIFICATE OF CORRECTION

PATENT NO. : 6,457,441 B1
DATED : October 1, 2002
INVENTOR(S) : Mitsuru Uchiyama It is certified that error appears in the above-identified patent and that said Letters Patent is hereby corrected as shown below:

Title page,
Item [57], ABSTRACT,
Line 2, "cable" should read -- capable --.
Line 14, "hat" should read -- that --.

Item [73], Assignee, please delete "Medical Clean Products Inc., Chiba (JP)".

Signed and Sealed this

Twenty-fifth Day of February, 2003

JAMES E. ROGAN
*Director of the United States Patent and Trademark Office*